United States Patent [19]

Zupon et al.

[11] Patent Number: 4,699,777

[45] Date of Patent: Oct. 13, 1987

[54] COMPOSITIONS AND METHOD FOR ENHANCEMENT OF THE TRANSDERMAL FLUX OF ALBUTEROL WITH A COMBINATION OF 1-DODECYL-AZACYCLOHEPTAN-2-ONE AND UREA

[75] Inventors: Michael A. Zupon, Madison, N.J.; Joel A. Sequeira, New York, N.Y.

[73] Assignee: Schering Corporation, Kenilworth, N.J.

[21] Appl. No.: 767,946

[22] Filed: Aug. 21, 1985

[51] Int. Cl.$^4$ .................. A61K 9/00; A61K 31/55; A61K 31/135
[52] U.S. Cl. .................... 424/28; 604/896; 514/653; 514/588; 514/202
[58] Field of Search ............... 574/653, 202, 588; 424/28; 604/896

[56] References Cited

U.S. PATENT DOCUMENTS

| 3,666,863 | 5/1972 | Swanbeck | 424/316 |
|---|---|---|---|
| 3,989,816 | 11/1976 | Rajadhyaksha | 574/24 |
| 4,164,564 | 8/1979 | Chin | 574/653 |
| 4,316,893 | 2/1982 | Rajadhyaksha | 574/24 |
| 4,557,934 | 12/1985 | Cooper | 574/270 |
| 4,568,343 | 2/1986 | Leeper et al. | 424/28 |

FOREIGN PATENT DOCUMENTS 1468815  3/1977  United Kingdom .

OTHER PUBLICATIONS

Seely et al., Salbutaval as a Topical Anti-inflammatory Drug, CA 90:48545s (1979).
Daikyo, Transserval Formulations Containing Urea, CA 99:58896g (1983).
Niho, Pharmaceuticals for External Application, CA 97:222960e (1982).
Rubin, Cosmetics and Toiletries, 91, 59 (Sep., 1976).
Stoughton, Arch Dermatol, 188, 474 (1982).
Stoughton, Azone ® (1-Dodecyl-Azacycloheptan-2-one) Enhances Percutaneous Penetration, III International Symposium on Psoriasis, Stanford, (Jul. 13-17, 1981).
Allenby et al., Brit. J. Dermatol., 81, Suppl. (4) 47-55 (1969).

Primary Examiner—Glennon H. Hollrah
Assistant Examiner—D. Dinner
Attorney, Agent, or Firm—Gerald S. Rosen; Stephen I. Miller; Thomas D. Hoffman

[57] ABSTRACT

A topical albuterol composition having superior transdermal flux containing various amounts of albuterol, 1-dodecyl-azacycloheptan-2-one and urea in a non-aqueous environment. The enhancement observed in albuterol skin penetration indicates that a therapeutically effective amount of albuterol can be delivered through skin using these formulations. The compositions can be administered topically as a cream, lotion or via a transdermal device.

14 Claims, No Drawings

COMPOSITIONS AND METHOD FOR ENHANCEMENT OF THE TRANSDERMAL FLUX OF ALBUTEROL WITH A COMBINATION OF 1-DODECYL-AZACYCLOPHEPTAN-2-ONE AND UREA

BACKGROUND OF THE INVENTION

This invention relates to a method for increasing the transdermal flux of albuterol and to compositions for effecting the method. The compositions of the invention, which greatly increase the transdermal flux of albuterol, comprise albuterol with a combination of 1-dodecyl-azacycloheptan-2-one and urea.

1-Dodecyl-azacycloheptan-2-one is registered under the U.S. Trademark "Azone" and is commercially available from Nelson Research and Development Company, Irvine, Calif.

Compositions and the method for preparation of the compound are disclosed in U.S. Pat. Nos. 3,989,815, and 4,316,893.

1-Dodecyl-azacycloheptan-2-one has properties which enhance the percutaneous absorption of certain chemical agents with which it is incorporated.

The use of suitable amounts of 1-dodecyl-azacycloheptan-2-one as a physiological carrier for topically administering an active agent to a human or animal is also disclosed in these patents, and discussed in Stoughton, *Azone* ® (*1-dodecyl-azacycloheptan-2-one*) *Enhances Percutaneous Penetration,* III International Symposium on Psoriasis, Stanford, (Jul. 13–17, 1981).

UK Pat. No. 1,468,815 discusses the use of urea in the treatment of skin conditions and restrictions on its use because it is unstable in neutral aqueous solution and decomposes, liberating carbon dioxide and ammonia. Urea buffered at a pH of about 2.0 has been tried, however, this very high acid level causes the cream containing said buffered urea to sting on application.

Further, urea, in an aqueous solution when adsorbed onto particles of an inert powder has been found to be sufficiently stable to be formulated into skin creams and other pharmaceutical preparations. U.S. Pat. No. 3,666,863 indicates that urea in aqueous solution has been used to enhance the topical absorption of compounds which have been known to have poor absorption.

The use of urea as a therapeutic agent for the treatment of hyperkeratotic skin conditions is disclosed in U.S. Pat. No. 3,666,863 and UK Pat. No. 1,468,815. In particular, urea is disclosed as being capable of hydrating the skin so as to allow the percutaneous transportation of medication, thus acting as a drug delivery system. A. C. Allenby, et al, *Mechanism of Action of Accelerants on Skin Penetration, Brit. J. Dermatol.,* Suppl. 81 (4), 47–55 (1969).

$\alpha^1$-[Tert-butylamino)methyl]-4-hydroxy-m-xylene $\alpha,\alpha'$-diol, also known as albuterol, is useful as a relatively selective beta-2 adrenergic bronchodilator. The rate and extent of albuterol diffusion through skin is slow and insufficient to be therapeutic from simple conventional formulations. This is so because albuterol does not possess the necessary physical-chemical characteristics of a molecule which is best suited for absorption from systemic topical application.

SUMMARY OF THE INVENTION

The present invention provides a method for enhancing skin penetration of albuterol in a mammal which comprises the administration of a composition comprising, a therapeutically effective amount of albuterol and a transdermal flux enhancing amount of a combination of 1-dodecyl-azacycloheptan-2-one and urea, with a pharmaceutically acceptable thickening agent. The composition of this invention comprises the following weight percent based on the total weight of the compositions:

(a) about 5 to 50 percent albuterol, preferably about 10 to 30 percent,
(b) about 5 to 50 percent 1-dodecyl-azacycloheptan-2-one, preferably about 10 to 50 percent,
(c) 5 to 50 percent urea, preferably 10 to 25 percent,
(d) sufficient pharmaceutically acceptable thickening agent to cause the formation of a homogeneous solid or semi-solid preparation, preferably polyvinyl chloride/vinyl acetate copolymer; mineral oil containing about 5 to 20 percent polyethylene; caprylic/capric triglyceride containing about 0.5 to 5 percent aluminum monostearate; isopropyl myristrate containing about 5 to 20 percent polyethylene.

The following compositions are preferred:

I. about 10% of albuterol; about 30% of 1-dodecyl-azacycloheptan-2-one; about 20% of urea; and about 40% polyvinyl chloride/vinyl acetate co-polymer.

II. about 30% of albuterol; about 35% of 1-dodecyl-azacycloheptan-2-one; about 20% of urea; and about 15% polyvinyl chloride/vinyl acetate co-polymer.

III. about 25% of albuterol; about 20% of 1-dodecyl-azacycloheptan-2-one; about 25% of urea; and about 30% polyvinyl chloride/vinyl acetate co-polymer.

IV. about 25% of albuterol; about 20% 1-dodecyl-azacycloheptan-2-one; about 20% of urea; and about 35% mineral oil containing about 5 to 20 percent polyethylene.

V. about 10% of albuterol; about 50% of 1-dodecyl-azacycloheptan-2-one; about 20% of urea; and about 20% caprylic/capric triglyceride containing about 0.5 to 5 percent aluminum monostearate.

VI. about 20% of albuterol; about 50% of 1-dodecyl-azacycloheptan-2-one; about 10% of urea; and about 20% isopropyl myristrate containing about 5 to 20 percent polyethylene.

VII. about 15% of albuterol; about 35% of 1-dodecyl-azacycloheptan-2-one; about 25% of urea; and about 25% polyvinyl chloride/vinyl acetate co-polymer.

The following compositions are most preferred:

VIII. about 20% of albuterol; about 35% of 1-dodecyl-azacycloheptan-2-one; about 20% of urea; and about 25% polyvinyl chloride/vinyl acetate co-polymer.

XI. about 20% of albuterol; about 35% of 1-dodecyl-azacycloheptan-2-one; about 20% urea; and about 25% polyvinyl chloride/vinyl acetate co-polymer.

DETAILED DESCRIPTION OF THE INVENTION

The invention provides a composition which can be administered topically as a cream, ointment or via a transdermal device, e.g., a patch. The patch is conveniently applied to the skin to provide transdermal albuterol administration over a prolonged period of time, e.g., about 24 hours to 168 hours. For reasons of convenience, effectiveness and controlled blood levels, the transdermal delivery via a patch of albuterol is preferred.

Preferably, the transdermal composition of this invention is utilized in a "reservoir type" or "matrix type"

patch which is applied to the skin and worn for a specific period of time to permit the absorption of a desired amount of albuterol through the skin. The compositions of this invention can be packaged to produce a "reservoir type" transdermal patch with or without a rate-limiting patch membrane. The size of the patch and/or the rate limiting membrane can be chosen to deliver the transdermal flux rates desired. The therapeutically desired transdermal amount of albuterol has been determined to be about 3 to 4 milligrams per day. *Drug Delivery Systems Characteristics and Biomedical Application;* R. L. Juliano, ed., Oxford University, N.Y. (1980); and *Controlled Drug Delivery Vol. 1 Basic Concepts,* Stephen D. Bruck (1983) describe the theory and application of methods useful for preparation of transdermal delivery systems. The relevant teachings of these texts are herein incorporated by reference. Thus, the drug-matrix could be formed by conventional means utilizing various polymers, e.g. silicone, polyvinyl alcohol, polyvinyl chloride-vinyl acetate co-polymer. The drug matrix is then packaged into an appropriate transdermal patch.

Pharmaceutically acceptable thickening agents are, for example, polyvinyl chloride/vinyl acetate copolymer, which is available under the trade name FPC 6338 from Occidental Chemical Corporation; mineral oil containing about 5 to 20 percent polyethylene (polyethylene is available under the trade name A-C ® Polyethylene from Allied Chemical Corporation); caprylic/capric triglyceride containing about 0.5 to 5 percent aluminum monostearate. Caprylic/capric triglyceride which is available under the tradename Miglyol ® from Dynamit Nobel; and isopropyl myristrate containing about 5 to 20 percent polyethylene.

These thickening agents result in a homogeneous semi-solid preparation and provide a medium through which the physiologically active agents can be applied to skin or be packaged into an appropriate "reservoir or matrix type" transdermal patch.

The following examples illustrate compositions of this invention and their preparation. All percentages therein are by weight. The definitions of components whose chemical compositions are not immediately clear from the name used, may be found in the CTFA Cosmetic Ingredients Dictionary, 3d Edition, published by the Cosmetic, Toiletry and Fragrance Association, Inc., Washington, D.C. It will be apparent to those skilled in the art that many modifications thereof may be practiced without departing from the purpose and intent of this invention.

PROCEDURE FOR EXAMPLES 1-13

1. Charge the 1-dodecyl-azacycloheptan-2-one to a suitable container.
2. Add the urea to the 1-dodecyl-azacycloheptan-2-one with appropriate agitation and mix until uniformly dispersed.
3. Add the albuterol with appropriate agitation and mix until uniformly dispersed.
4. Charge the thickening agent and mix until uniformly dispersed.
5. Cure the drug/polymer mixture, if necessary, and then form, fill and seal the formulation to yield a transdermal drug delivery system.

SCREENING OF ALBUTEROL FOR TRANSDERMAL PENETRATION

Compositions containing albuterol, Azone ® and urea were screened for transdermal penetration as follows:

The skin diffusion cells used were similar to those described by Franz, J. Invest. Derm., 64,190, (1975). Excised defatted human skin was stretched across a reservoir containing a phosphate buffer solution (pH 7.4, 0.02M) in direct contact with the dermal side of the skin. The temperature of this buffer solution was maintained at 37° ±0.5° C. by circulating water at the appropriate temperature through a jacket which surrounds each assembly. Freshly made albuterol preparations were applied to the stratum corneum surface. The buffer solution was removed in its entirety and replaced with fresh solution at various time intervals and assayed for albuterol content in order to determine albuterol flux through skin.

Table II shows that 1-dodecyl-azacycloheptan-2-one when incorporated into an albuterol non-aqueous polymeric matrix, enhances the transdermal flux of albuterol through human cadaver skin in a dose dependent manner.

Table III shows that a 1-dodecyl-azacycloheptan-2-one and urea combination enhances the transdermal flux of albuterol to a greater extent than do equivalent concentrations of 1-dodecyl-azacycloheptan-2-one or urea used alone.

In particular, urea and 1-dodecylazacycloheptan-2-one in combination within an albuterol:non-aqueous vehicle, when applied to skin or membrane surfaces, causes an absorption rate of albuterol greater than that resulting from its use with urea or 1-dodecyl-azacycloheptan-2-one alone and greater than an additive effect of the urea and Azone. In fact, greater absorption of albuterol has been achieved than has heretofore been

TABLE 1

Transdermal Pharmaceutical Compositions of the Present Invention (Examples 1-13)

| | Percent By Weight | | | | | | | | | | | | |
|---|---|---|---|---|---|---|---|---|---|---|---|---|---|
| Ingredients | Ex 1 | Ex 2 | Ex 3 | Ex 4 | Ex 5 | Ex 6 | Ex 7 | Ex 8 | Ex 9 | Ex 10 | Ex 11 | Ex 12 | Ex 13 |
| Albuterol | 5 | 20 | 50 | 40 | 25 | 10 | 20 | 20 | 15 | 10 | 30 | 25 | 20 |
| 1-dodecylazacycloheptan-2-one | 35 | 35 | 15 | 5 | 20 | 50 | 50 | 35 | 35 | 30 | 35 | 20 | 50 |
| Urea | 20 | 20 | 20 | 25 | 20 | 20 | 5 | 20 | 25 | 20 | 20 | 25 | 10 |
| Polyvinyl Chloride Vinyl Acetate Co-polymer | 40 | 25 | 15 | 30 | 0 | 0 | 0 | 25 | 25 | 40 | 15 | 30 | 0 |
| Mineral Oil containing 5 to 20 percent polyethylene | 0 | 0 | 0 | 0 | 35 | 0 | 0 | 0 | 0 | 0 | 0 | 0 | 0 |
| Caprylic/capric triglyeride containing 0.5 to 5 percent alumninum monostearate | 0 | 0 | 0 | 0 | 0 | 20 | 0 | 0 | 0 | 0 | 0 | 0 | 0 |
| Isopropyl Myristrate containing 5 to 20 percent polyethylene | 0 | 0 | 0 | 0 | 0 | 0 | 25 | 0 | 0 | 0 | 0 | 0 | 20 | possible. It is also surprising that urea is effective for this use when in non-aqueous form.

The result is that the albuterol:1-dodecyl-azacycloheptan-2-one:urea composition having enhanced skin absorption properties, delivers a therapeutically effective amount of albuterol through the skin.

TABLE II

| IN VITRO SKIN PENETRATION | | | |
|---|---|---|---|
| | | Cumulative Albuterol Flux[a] (mg/cm$^2$) | |
| Formulation | n[b] | 24 hour | 48 hour |
| Alb:PVC/VA[c] (30:70) | 4 | 0 | 0 |
| Alb:Azone:PVC/VA (30:10:60) | 3 | 0.01 | 0.04 |
| Alb:Azone:PVC/VA (30:25:45) | 3 | 0.02 | 0.14 |
| Alb:Azone:PVC/VA (30:50:20) | 3 | 0.04 | 0.36 |

[a]Flux through human cadaver skin. Skin:female, non-white, 79. Mean of n diffusion cells
[b]Number of skin diffusion cells.
[c]PVC/VA:polyvinyl chloride/vinyl acetate co-polymer.

Table II shows cumulative albuterol flux rates when varying levels of Azone® are incorporated into an albuterol: non-aqueous polymeric matrix, e.g., polyvinyl chloride/vinyl acetate co-polymer. These data show the enhancement of albuterol flux by Azone® through human cadaver shin in a dose dependent manner.

TABLE III

| In Vitro Skin Penetration | | | |
|---|---|---|---|
| | | Cumulative Albuterol Flux[a] (mg/cm$^2$) | |
| Formulation | n[b] | 24 hour | 48 hour |
| Alb:Urea:PVC/VA[c] (20:20:60, w:w:w) | 3 | 0.05 | 0.28 |
| Alb:Azone:PVC/VA (20:50:30, w:w:w) | 3 | 0.08 | 0.65 |
| Alb:Azone:Urea:PVC/VA (20:15:20:45, w:w:w:w) | 3 | 0.13 | 0.53 |
| Alb:Azone:Urea:PVC/VA (20:25:20:35, w:w:w:w) | 3 | 0.13 | 0.64 |
| Alb:Azone:Urea:PVC/VA (20:35:20:25, w:w:w:w) | 4 | 0.37 | 1.32 |

[a]Flux through human cadaver skin. Skin:female, white, 62. Mean of n diffusion cells
[b]Number of skin diffusion cells.
[c]PVC/VA:polyvinyl chloride/vinyl acetate co-polymer.

Table III illustrates a more than additive increased enhancement of albuterol transdermal absorption when urea is incorporated into the albuterol:Azone®; polymeric matrix. This Azone®/urea combination enhances the transdermal absorption of albuterol to a greater extent than do comparable concentrations of Azone® or urea when used alone.

What is claimed is:

1. A method of enhancing the transdermal absorption of albuterol to an extent greater than the additive effects of 1-dodecyl-azacycloheptan-2-one and urea which comprises topically applying a composition comprising as the pharmaceutically active component, a therapeutically effective amount of albuterol and a combination of, based on the total weight of the composition, about 5 to 50% of 1-dodecyl-azacycloheptan-2-one and 5 to 50% of non-aqueous urea, with sufficient amount of a pharmaceutically acceptable thickening agent to cause the formation of a homogeneous solid or semi-solid preparation.

2. A topical pharmaceutical composition which enhances the transdermal absorption of albuterol to an extent greater than the additive effects of 1-dodecyl-azacylcoheptan-2-one and urea which comprises a therapeutically effective asount of albuterol in combination with, based on the total weight of the composition, about 5 to 50% non-aqueous urea and about 5 to 50% 1-dodecyl-azacycloheptan-2-one, and sufficient amount of a pharmaceutically acceptable thickening agent to cause the formation of a homogeneous solid or semi-solid preparation.

3. A composition of claim 2 which is formulated as a cream.

4. A composition of claim 2 which is formulated as an ointment.

5. A composition of claim 2 having about 5 to 50% albuterol by weight.

6. A composition of claim 2 comprising by percent weight:
about 10% of albuterol;
about 30% of 1-dodecyl-azacycloheptan-2-one;
about 20% of non-aqueous urea; and wherein said thickening agent comprises about 40% polyvinyl chloride/vinyl acetate co-polymers.

7. A composition of claim 2 comprising by percent weight:
about 20% of albuterol;
about 35% of 1-dodecyl-azacycloheptan-2-one;
about 20% of non-aqueous urea; and
wherein said thickening agent comprises about 25% polyvinyl chloride/vinyl acetate co-polymer.

8. A composition of claim 2 comprising by percent weight:
about 30% of albuterol;
about 35% of 1-dodecyl-azacycloheptan-2-one;
about 20% of non-aqueous urea; and
wherein said thickening agent comprises about 15% polyvinyl chloride/vinyl acetate co-polymer.

9. A composition of claim 2 comprising by percent weight:
about 25% of albuterol;
about 20% of 1-dodecyl-azacycloheptan-2-one;
about 25% of non-aqueous urea; and
wherein said thickening agent comprises about 30% polyvinyl chloride/vinyl acetate co-polymer.

10. A composition of claim 2 comprising by percent weight:
about 25% of albuterol;
about 20% 1-dodecyl-azacycloheptan-2-one;
about 20% of non-aqueous urea; and
wherein said thickening agent comprises about 35% mineral oil containing about 5 to 20 percent polyethylene.

11. A composition of claim 2 comprising by percent weight:
about 10% of albuterol;
about 50% of 1-dodecyl-azacycloheptan-2-one;
about 20% of non-aqueous urea; and
wherein said thickening agent comprises about 20% caprylic/capric triglyceride containing about 0.5 to 5 percent aluminum monostearate.

12. A composition of claim 2 comprising by percent weight:
about 20% of albuterol;
about 50% of 1-dodecyl-azacycloheptan-2-one;
about 10% of non-aqueous urea; and
wherein said thickening agent comprises about 20% isopropyl myristrate containing about 5 to 20 percent polyethylene.

13. A composition of claim 2 comprising by percent weight:
about 20% of albuterol;
about 35% of 1-dodecyl-azacycloheptan-2-one;
about 20% urea; and
about 25% polyvinyl chloride/vinyl acetate co-polymer 14. The composition of claim 2 comprising by percent weight:
about 15% of albuterol;
about 35% of 1-dodecyl-azacycloheptan-2-one;
about 25% of non-aqueous urea; and wherein said thickening agent comprises about 25% polyvinyl chloride/vinyl acetate co-polymer.

* * * * *